United States Patent
Van Den Enden et al.

(10) Patent No.: US 10,349,612 B2
(45) Date of Patent: Jul. 16, 2019

(54) HAIRLESS EGGPLANT

(71) Applicant: RIJK ZWAAN ZAADTEELT EN ZAADHANDEL B.V., De Lier (NL)

(72) Inventors: Johannes Henricus Jacobus Van Den Enden, De Lier (NL); Christine Helene Diez Langhetee, De Lier (NL); Maria Teresa Perez Rodriguez, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 14/628,169

(22) Filed: Feb. 20, 2015

(65) Prior Publication Data

US 2015/0164014 A1 Jun. 18, 2015

Related U.S. Application Data

(63) Continuation-in-part of application No. PCT/EP2013/067555, filed on Aug. 23, 2013.

(30) Foreign Application Priority Data

Aug. 23, 2012 (EP) ..................... 12181582

(51) Int. Cl.
*A01H 6/82* (2018.01)
*A01H 5/08* (2018.01)
*A01H 5/04* (2018.01)
*A01H 5/12* (2018.01)

(52) U.S. Cl.
CPC ............... *A01H 6/826* (2018.05); *A01H 5/04* (2013.01); *A01H 5/08* (2013.01); *A01H 5/12* (2013.01)

(58) Field of Classification Search
None
See application file for complete search history.

(56) References Cited

PUBLICATIONS

Javed et al. (Pak. J. Bot., 43(4): 2023-2028, 2011).*
Sekara et al. (Folia Horticulturae, Ann. 19/1, 2007, 97-114).*
Sadilova et al. Zeitschrift für Naturforschung C 61.7-8 (2006): 527-535. (Year: 2006).*
Kirk et al. Plant Molecular Biology 55:389-398, 2004. (Year: 2004).*
Fu et al. Photosynthetica 51 (1): 109-114, 2013. (Year: 2013).*
Boo et al. (HortScience 45.5 (2010): 775-777). (Year: 2010).*
Mukherjee et al. (Plant cell, tissue and organ culture 25.1 (1991): 13-16). (Year: 1991).*
International Search Report dated Nov. 21, 2013, which issued during prosecution of International Application No. PCT/EP2013/067555.
Muhammad Ali, et al. "The Physio-Morphic Characters of the Brinjal (*Solanum melongena* L.) Plant and Their Relationship with the Jassid (*Amrasca biguttula biguttula* (Ishida) Population Fluctuation" Pak. J. Agri. Sci. 49 (1):67-71, Jan. 2012.
Anonymous, "African eggplant" AVRDC Library Online, pp. 230-233, Aug. 24, 2009, retrieved from the Internet: http://libnts.avrdc.org.tw/fulltext_pdf/ebook/10-51%20african%20eggplant.pdf (retrieved on Jan. 10, 2013).
R. Ayyasamy, et al. "Influence of certain leaf characters of brinjal accessions with incidence of Bemisia tabaci" Journal of Food, Agriculture & Environment 3(2):333-334, Apr. 2005.
Humayun Javed, et al. "Relationship between Morphological Characters of Different Aubergine Cultivars and Fruit Infestation by Leucinodes Orbonalis Guenee" Pakistan Journal of Botany 43(4):2023-2028, Aug. 2011.
International Preliminary Report on Patentability and Written Opinion of the International Searching Authority dated Feb. 24, 2015, which issued during prosecution of International Application No. PCT/EP2013/067555.
Daunay, et al. "Genetic Resources of Eggplant (*Solanum melongena*) and Allied Species: A New Challenge for Molecular Geneticists and Eggplant Breeders" Solanaceae V Advances in Taxonnomy and Utilization, 2001, 5:251-274.

* cited by examiner

*Primary Examiner* — Elizabeth F McElwain
*Assistant Examiner* — Charles Logsdon
(74) *Attorney, Agent, or Firm* — Duane Morris LLP; Thomas J. Kowalski; Deborah L. Lu

(57) ABSTRACT

The present invention relates to an eggplant, in particular a *Solanum melongena* plant, comprising a genetic determinant, which when present confers a reduced number of trichomes on vegetative plant parts, and which is as found in plants grown from seed of which representative samples were deposited under NCIMB accession numbers NCIMB 41756 and NCIMB 42013. When the genetic determinant is homozygously present the number of trichomes is strongly reduced.

10 Claims, 2 Drawing Sheets

HAIRLESS EGGPLANT

RELATED APPLICATIONS AND INCORPORATION BY REFERENCE

This application is a continuation-in-part application of international patent application Serial No. PCT/EP2013/067555 filed 23 Aug. 2013, which published as PCT Publication No. WO 2014/029876 on 27 Feb. 2014, which claims benefit of European patent application Ser. No. 12181582.3 filed 23 Aug. 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a novel eggplant (*Solanum melongena* L.) which facilitates the application of biological pest control and leads to a lower risk of skin irritation. The invention further relates to the seeds and progeny of such plants and to propagation material for obtaining such plants. Furthermore the invention relates to the use of plants, seeds and propagation material derived from such plants as germplasm in a breeding program.

BACKGROUND OF THE INVENTION

The eggplant, or aubergine, (*Solanum melongena* L.) is a plant of the nightshade family (Solanaceae) and belongs to the genus *Solanum*. It is closely related to tomato and potato. The eggplant bears a fruit of the same name, commonly used in cooking. It is an important food crop, grown worldwide in all conditions and climates both in protected cultivation and in the open field. The stem is often spiny or pubescent. The leaves are hairy and sometimes the calyx shows some small spines. All the vegetative parts of an eggplant are more or less densely pubescent with stellate trichomes, the trichomes give a greyish or purplish-greenish appearance.

The surface of the various plant parts of the eggplant is covered with star-shaped trichomes with one vertical and two to eight horizontal arms.

Trichomes are fine outgrowths or appendages on plants. These can exist in diverse structure and function. Examples are hairs, glandular hairs, scales, and papillae. Plant trichomes have various functions, ranging from the inhibition of dehydration to being a mechanical barrier against small herbivorous animals and insects.

However, leaf trichomes do not only affect pest insects, but also the natural enemies of the pest insects. This may again affect the intensity of damage caused by pest insects. In theory, the effect of trichomes on the abundance and effectiveness of the pest and the natural enemies of the pest may be neutral, negative or positive. The effectiveness of both predators and pest insects can be affected because movement may be inhibited and search time could be prolonged by the presence of trichomes. It is a first object of the present invention to provide an eggplant that facilitates the natural enemies of pest insects.

Growing plants like eggplants, peppers and tomato requires a lot of manual labor. Handling plants involves grafting, planting, pruning, winding, and harvesting. Workers in the horticultural sector are not only exposed to inhalation of dust and pollen from plants, but also to skin contact with other plant parts and various kind of chemical compounds excreted by plants. In general, sensitivity to pollen, dust and other parts of plants is a growing problem in horticulture. It was found that also eggplant can cause such sensitivity reactions in people working with the plants.

Citation or identification of any document in this application is not an admission that such document is available as prior art to the present invention.

SUMMARY OF THE INVENTION

It is therefore a further object of the invention to provide an eggplant that does not cause sensitivity reactions.

There is thus a need to develop an eggplant not having the ability to cause mentioned sensitivity reactions in human skin. Furthermore, there is a need for an eggplant that facilitates the application of biological pest control During experiments that lead to the present invention it was found that an eggplant with a genetic determinant that causes a reduced number of trichomes is beneficial for the application in biological pest control. Furthermore it was found that an eggplant with this genetic determinant also causes less sensitivity reactions in human skin.

The invention relates to an eggplant, which may comprise a genetic determinant which when present leads to a trait of a reduced number of trichomes on vegetative plant parts, in particular leafs, stems and calyx, as compared to a plant not comprising the said genetic determinant, and wherein the genetic determinant is the same as or equivalent to a genetic determinant present in the genome of plants grown from seed which were deposited under accession numbers NCIMB 41756 and NCIMB 42013.

The invention also relates to an eggplant (*Solanum melongena* L.) which may comprise a genetic determinant which when present leads to a reduced number of trichomes on vegetative plant parts, in particular leafs, stems and calyx, as compared to a plant not comprising the said genetic determinant, and which genetic determinant is as present in plants grown from seed of which representative samples were deposited under accession numbers NCIMB 41756 and NCIMB 42013.

The invention also provides an eggplant of the species *Solanum melongena* which has a reduced number of trichomes on vegetative plant parts, in particular leafs, stems and calyx, as compared to a control plant, which plant is obtainable by crossing an eggplant of NCIMB 41756 or NCIMB 42013 with another eggplant and selecting in the first or further progeny of the cross for plants having a reduced number of trichomes.

The eggplant seed which may comprise the genetic determinant which when present leads to a reduced number of trichomes on vegetative plant parts, has been deposited on 22 September 2010 at the NCIMB in Aberdeen under accession number NCIMB 41756 and on 19 July 2012 at the NCIMB under accession number NCIMB 42013. The deposits do not fulfill the requirements of uniformity and stability and therefore they do not constitute a plant variety.

The invention relates also to an eggplant which may comprise a genetic determinant which when present leads to a reduced number of trichomes on vegetative plant parts except for the root, fruits and reproductive organs, as compared to an eggplant not comprising the said genetic determinant. The "reduced number of trichomes on vegetative plant parts" is intended to mean a reduced number of trichomes on at least one, preferably most, more preferably all vegetative plant parts.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

The Deposits with NCIMB Ltd. (Ferguson Building, Craibstone Estate, Bucksburn, Aberdeen, AB21 9YA), under deposit accession number NCIMB 41756 and NCIMB 42013 were made pursuant to the terms of the Budapest Treaty. Upon issuance of a patent, all restrictions upon the deposit will be removed, and the deposit is intended to meet the requirements of 37 CFR 37 CFR §§ 1.801-1.809. The deposit will be irrevocably and without restriction or condition released to the public upon the issuance of a patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
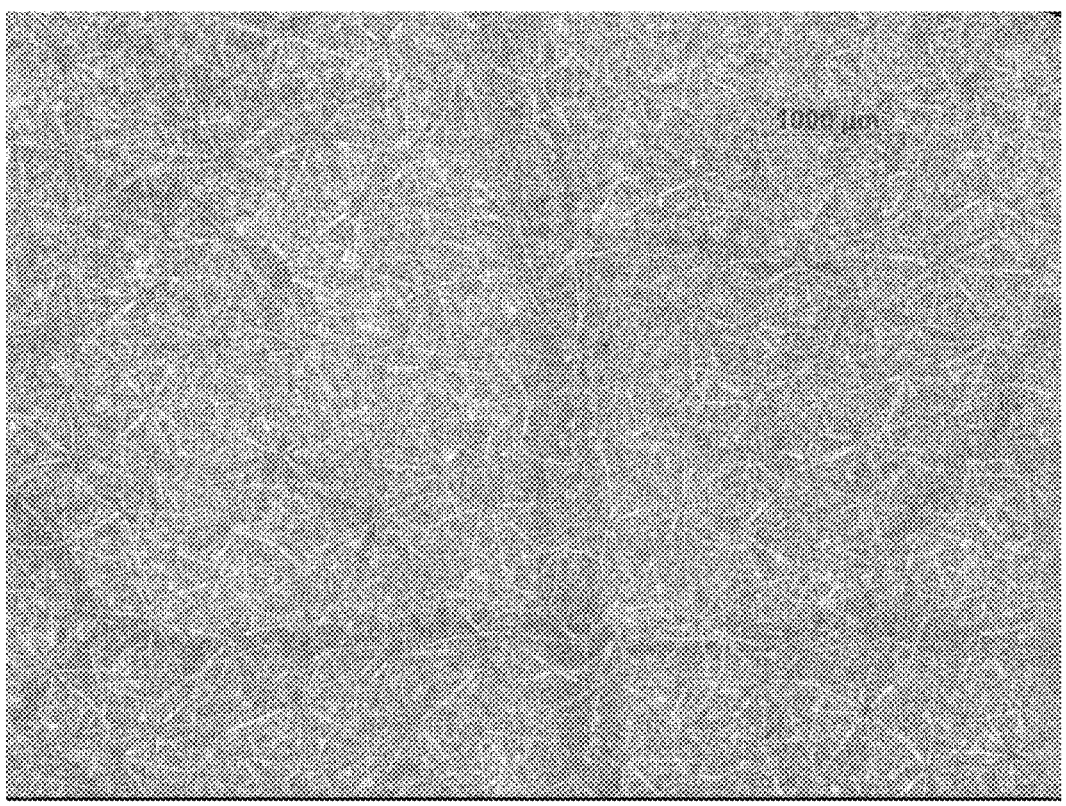
FIG. 1 Photograph of a leaf with normal trichome density.

The definition "vegetative plant parts" as used in this application is intended to mean the aboveground parts of the plant that are not directly involved in sexual reproduction, including but not exclusively leaves, stems, calyx/sepals, flower petals and shoots. Plant parts like roots, stamen, pistils, and the fruits of eggplants in general do not have any trichomes.

The word trichomes as used in this application is intended to mean both stellate and simple fine outgrowths or appendages on eggplants, on stems, leafs, etc. Trichomes exist in diverse structure and function. Examples are hairs, glandular hairs, scales, and papillae. Trichomes can be used as a synonym for hairs but cover more structures than only hairs. Plant trichomes have various functions, ranging from the inhibition of dehydration and being a mechanical barrier against small herbivorous animals and insects. The spines and thorns occasionally found in certain eggplants on calyx, main stem and major veins of leafs are not considered as trichomes as defined herein. The reduced number of trichomes can also be described as a reduction of trichomes, a low density of trichomes, absence of trichomes, a low number of trichomes, or scarcity of trichomes.

Preferably, the genetic determinant is homozygously present. When the said genetic determinant is homozygously present, the plants will show a strongly reduced number of trichomes. Compared to plants not having the genetic determinant the number of trichomes on vegetative plant parts of the plants which may comprise the genetic determinant are reduced. Plants which may comprise the genetic determinant in heterozygous state will show an intermediate level of trichome density. This means that plants having the determinant in heterozygous state will still show a reduced number of trichomes as compared to plants not having the determinant and an increased number of trichomes as compared to plants having the genetic determinant in a homozygous state.

The invention also relates to an eggplant, which may comprise a genetic determinant which when present leads to a reduced number of trichomes on vegetative plant parts as compared to a plant not comprising the said genetic determinant, and which genetic determinant is the same as or equivalent to a genetic determinant that is as present in plants grown from seed, representative samples of which were deposited under accession numbers NCIMB 41756 and NCIMB 42013, wherein the plant is obtainable by crossing a first eggplant not having the genetic determinant, with a second eggplant having the genetic determinant, or by introgression of the genetic determinant into the first eggplant from the second eggplant, wherein the genetic determinant is as present in plants grown from seed, representative samples of which were deposited under accession numbers NCIMB 41756 and NCIMB 42013.

The eggplant of the invention is preferably a *Solanum melongena* plant, but can also be another related plant of the so-called eggplant complex within the genus *Solanum*, like *S. aethiopicum, S. incanum, S. macrocarpon* and *S. linnaeanum*, into which the skilled person can introgress the genetic determinant of the invention. The invention relates to plants of these species that have the genetic determinant causing a reduced number of trichomes as found in the deposit. The skilled person knows how to make (interspecific) crosses with these species, e.g. by means of embryo rescue, protoplast fusion, and other related technologies. Preferably, the invention is used in plant species that produce edible fruits. The preferred plant species for use with this invention is *Solanum melongena*.

Introgression as used herein is intended to mean the introduction of a certain trait or a certain genetic determinant causing said trait, into a plant not carrying the trait nor the genetic determinant, by means of one or several repeating steps of crossing and selection.

Eggplants carrying the said genetic determinant leading to the trait strongly reduced number of trichomes on vegetative plant parts can suitably be identified among descendants from a cross between a plant not comprising the genetic determinant, and a plant which may comprise the genetic determinant in homozygous state, by growing F2 plants from seeds that are the result from the initial cross and a selfing step, and selecting plants showing the desired trait. Selecting the plants can be done phenotypically, or can be done through identification of the genetic determinant, for example by means of one or more molecular markers. Markers can be developed accordingly based on the material that was deposited under number NCIMB 41756 or NCIMB 42013 by a skilled person.

Equivalence of genetic determinants can be determined by an allelism test. To perform an allelism test, material that is homozygous for the known determinant, a tester plant, is crossed with material that is homozygous for the genetic determinant that is to be tested. This latter plant is referred to as the donor plant. The donor plant to be tested should be or should be made homozygous for the genetic determinant to be tested. The skilled person knows how to obtain a plant that is homozygous for the genetic determinant to be tested. When in the F2 of the cross between a donor plant and a tester plant no segregation for the phenotype related to the genetic determinant is observed, the genetic determinants of the donor plant and the tester plant have been proven to be equivalent or the same.

The present invention thus relates to an eggplant that may comprise a genetic determinant causing a reduced number of trichomes on vegetative plant parts, wherein plants of first generation progeny (F1) of a cross of the eggplant carrying the said genetic determinant with a tester plant, that may comprise the said genetic determinant and of which representative seed was deposited with the NCIMB under accession numbers NCIMB 41756 and NCIMB 42013, or a progeny plant thereof that may comprise the said genetic determinant, or a plant derived therefrom and which may comprise the said genetic determinant, show a 1:0 segregation for the said trait. In both the tester plant and the plant of the invention the genetic determinant is present in homozygous form. Plants of the second and further generations, if obtained by selfing also show a 1:0 segregation for the said trait. The tester plant can be a plant of which representative seed was deposited with the NCIMB under accession number NCIMB 41756 and number NCIMB 42013.

The invention relates to an eggplant, which may comprise a genetic determinant which when present leads to a reduced number of trichomes on vegetative plant parts, in particular leafs, stems and calyx, as compared to a plant not comprising the said genetic determinant, and which genetic determinant is as present in plants grown from seed, representative samples of which were deposited under accession numbers NCIMB 41756 and NCIMB 42013, and wherein the leaf blade/lamina of the mature leaves of the eggplant has less than 130 trichomes per square centimeter, preferably less than 120 trichomes per square centimeter, more preferably less than 110 trichomes per square centimeter, even more preferably less than 100 trichomes per square centimeter, even more preferably less than 90 trichomes per square centimeter, even more preferably less than 80 trichomes per square centimeter, even more preferably less than 70 trichomes per square centimeter, even more preferably less than 60 trichomes per square centimeter, even more preferably less than 50 trichomes per square centimeter, even more preferably less than 40 trichomes per square centimeter, even more preferably less than 30 trichomes per square centimeter, even more preferably less than 20 trichomes per square centimeter, even more preferably less than 10 trichomes per square centimeter, most preferably 0.

Most angiosperm plants have leaves that may comprise of a leaf blade (also called lamina), a leaf stalk (also called petiole), and stipules. An eggplant leaf consists of a leaf blade/lamina and a leaf stalk/petiole. The leaf blade is the largest mostly flat broad part of the leaf and it is attached to the main stem via the leaf stalk. The leaf stalk is the smallest part of a leaf that connects the leaf blade with the main stem of the plant.

Mature eggplant leaves as defined in the current application are leaves that are fully stretched. For the trichome counts, as illustrated in example 1, a sample of the mature leaf was taken from the first stretched leaf seen from the top of the plant. In general this was the third leaf under the leaf that was defined as young leaf. Furthermore, young eggplant leaves as defined in the current application are leafs that are not yet fully stretched. For the trichome counts, illustrated in example 1, the samples of the young leaf were taken from the first leaf from the top of the plant that measured 5 centimeter in length.

The invention also relates to an eggplant, which may comprise a genetic determinant which when present leads to a reduced number of trichomes on vegetative plant parts, as compared to a plant not comprising the said genetic determinant, and which genetic determinant is as found in plants grown from seed of which a representative sample was deposited with the NCIMB under accession number NCIMB 41756 and NCIMB 42013, and wherein the leaf blade of young leafs of the eggplant has less than 400 trichomes per square centimeter, preferably less than 390 trichomes per square centimeter, more preferably less than 380 trichomes per square centimeter, even more preferably less than 370 trichomes per square centimeter, even more preferably less than 360 trichomes per square centimeter, even more preferably less than 350 trichomes per square centimeter, even more preferably less than 340 trichomes per square centimeter, even more preferably less than 330 trichomes per square centimeter, even more preferably less than 320 trichomes per square centimeter, even more preferably less than 310 trichomes per square centimeter, even more preferably less than 300 trichomes per square centimeter, even more preferably less than 290 trichomes per square centimeter, even more preferably less than 280 trichomes per square centimeter, even more preferably less than 270 trichomes per square centimeter, even more preferably less than 260 trichomes per square centimeter, even more preferably less than 250 trichomes per square centimeter, even more preferably less than 240 trichomes per square centimeter, even more preferably less than 230 trichomes per square centimeter, even more preferably less than 220 trichomes per square centimeter, even more preferably less than 210 trichomes per square centimeter, even more preferably less than 200 trichomes per square centimeter, even more preferably less than 190 trichomes per square centimeter, even more preferably less than 180 trichomes per square centimeter, even more preferably less than 170 trichomes per square centimeter, even more preferably less than 160 trichomes per square centimeter, even more preferably less than 150 trichomes per square centimeter, even more preferably less than 140 trichomes per square centimeter, even more preferably less than 130 trichomes per square centimeter, even more preferably less than 120 trichomes per square centimeter, even more preferably less than 110 trichomes per square centimeter, even more preferably less than 100 trichomes per square centimeter, even more preferably less than 90 trichomes per square centimeter, even more preferably less than 80 trichomes per square centimeter, even more preferably less than 70 trichomes per square centimeter, even more preferably less than 60 trichomes per square centimeter, even more preferably less than 50 trichomes per square centimeter, even more preferably less than 40 trichomes per square centimeter, even more preferably less than 30 trichomes per square centimeter, even more preferably less than 20 trichomes per square centimeter, even more preferably less than 10 trichomes per square centimeter, most preferably 0.

The invention also relates to an eggplant, which may comprise a genetic determinant which when present leads to a reduced number of trichomes on vegetative plant parts, as compared to a plant not comprising the said genetic determinant, and which genetic determinant is as found in plants grown from seed of which a representative sample is deposited with the NCIMB under accession number NCIMB 41756 or NCIMB 42013, and wherein the main stems of the eggplant have less than 4 trichomes per square centimeter, preferably less than 3 trichomes per square centimeter, more preferably less than 2 trichomes per square centimeter, even more preferably less than 1 trichome per square centimeter, even more preferably less than 0.5 trichome per square centimeter, most preferably 0.

The invention relates to trichome counts in the eggplants in mature leaves that are made on 1 square centimeter on the underside of the leaf blade/lamina, on the upperside of the leaf stalk/petiole of the leaf, in young leaves on the underside of both leaf blade and petiole, and on the main stem. The counts that are mentioned are based on average counts on 5 individual eggplant plants, each count made twice for each plant part. Individual counts that would diverge from these averages are possible.

One embodiment of the invention relates to seed which may comprise the genetic determinant which when present leads to a trait of a reduced number of trichomes on vegetative plant parts in a plant grown from said seed as compared to a plant grown from seed not comprising the genetic determinant, and wherein the genetic determinant is as found in plants grown from seed of which representative samples have been deposited under accession numbers NCIMB 41756 and number NCIMB 42013. If the said seed comprises the genetic determinant in a homozygous state, the plant grown from the seed will show a strongly reduced number of trichomes compared to a plant grown from seed not comprising the genetic determinant. If the said seed comprises the genetic determinant in a heterozygous state, the plant grown from said seeds will show a reduced number of trichomes compared to a plant grown from seed not comprising the genetic determinant and an increased number of trichomes compared to plant grown from seed which may comprise the genetic determinant in a homozygous state.

In one embodiment the invention relates to a progeny plant of an eggplant which may comprise the genetic determinant which when present leads to a reduced number of trichomes on vegetative plant parts, compared to an eggplant not comprising the genetic determinant, wherein the progeny plant of said eggplant may comprise the genetic determinant.

Another embodiment of the invention relates to a progeny plant of an eggplant which may comprise the genetic determinant which when present leads to a reduced number of trichomes on vegetative plant parts, compared to an eggplant not comprising the genetic determinant, wherein the progeny plant of said eggplant may comprise the genetic determinant homozygously.

The definition of progeny as used in this application is intended to mean the first and all further descendants from a cross with a plant of the invention that shows the discussed trait, in this particular case the reduced number of trichomes on vegetable parts of the eggplant. The term "progeny" also encompasses plants that carry the trait of the invention and are obtained from other plants or progeny of plants of the invention by vegetative propagation or multiplication.

The invention relates to propagation material derived from an eggplant which may comprise the genetic determinant which when present leads to a reduced number of trichomes on vegetative plant parts as compared to an eggplant not comprising said genetic determinant, wherein the propagation material may comprise the genetic determinant.

The invention relates to propagation material capable of growing into an eggplant which may comprise the genetic determinant which when present leads to a reduced number of trichomes on vegetative plant parts as compared to an eggplant not comprising said genetic determinant, wherein the propagation material may comprise the genetic determinant.

The propagation material can be selected from the group consisting of microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts thereof.

Another aspect of the invention relates to tissue culture of said propagation material.

The invention furthermore relates to a method for the production of an eggplant which may comprise the trait of a reduced number of trichomes on vegetative plant parts by using a method for genetic modification to introgress the said trait into an eggplant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

In another embodiment the invention relates to an eggplant fruit, or parts thereof, or a food product made of a fruit or of parts thereof, or a processed food product made thereof, harvested from an eggplant which may comprise the genetic determinant which when present leads to a reduced number of trichomes on vegetative plant parts, as compared to an eggplant not comprising said genetic determinant, and which genetic determinant is as present in plants grown from seed, representative samples of which were deposited under accession numbers NCIMB 41756 and NCIMB 42013. Even though the trait of the invention may no longer be visible on the fruit parts or processed forms thereof, such materials still may comprise the genetic determinant underlying the trait and are thus still a part of the invention.

The invention further relates to the use of an eggplant, which may comprise a genetic determinant which when present leads to a reduced number of trichomes on vegetative plant parts as compared to an eggplant not comprising said genetic determinant, as germplasm in a breeding program for the development of eggplants which may comprise a genetic determinant that leads to a reduced number of trichomes on vegetative parts of the plant, as compared to a plant not carrying said determinant.

In one aspect the invention relates to a method for production of an eggplant which may comprise a genetic determinant which when present leads to the trait of a reduced number of trichomes on vegetative plant parts, in particular leafs, stems and calyx, as compared to a plant not comprising the said genetic determinant, and which genetic determinant is as present in plants grown from seed, representative samples of which were deposited under accession numbers NCIMB 41756 and NCIMB 42013, which may comprise:

a) crossing a plant which may comprise a genetic determinant that leads to the trait with another plant;
b) selfing the resulting F1 for obtaining F2 plants;
c) selecting plants that have the trait in the F2;
d) optionally performing one or more additional rounds of selfing or crossing, and subsequently selecting, for a plant comprising/showing the trait.

The word "trait" in the context of this application refers to the phenotype of the plant. The term "genetic determinant" is used for the genetic information in the genome of the plant that causes the trait. When a plant shows the trait of the invention, its genome may comprise the genetic determinant causing the trait of the invention. The plant thus has the genetic determinant of the invention. The genetic determinant can be a gene, a complex of multiple genes, an allele, etc.

It is clear that the parent that provides the trait of the invention is not necessarily a plant grown directly from the deposited seeds. The parent can also be a progeny plant from the seed or a progeny plant from seeds, that are identified to have the trait of the invention by other means, and has in particular the genetic determinant that causes the trait.

In one aspect, the invention relates to a method for production of an eggplant which may comprise a genetic determinant which when present leads to a trait of a reduced number of trichomes on vegetative plant parts, as compared to a plant not comprising the said genetic determinant, and which genetic determinant is as present in plants grown from seed, of which representative samples were deposited under accession numbers NCIMB 41756 and NCIMB 42013, comprising:

a) crossing a plant comprising the genetic determinant that leads to the trait with another plant;
b) optionally backcrossing the resulting F1 with the preferred parent;
c) selecting for plants that have the trait in the F2;
d) optionally performing one or more additional rounds of selfing or crossing, and subsequently selecting, for a plant comprising the trait.

The invention additionally provides a method of introducing another desired trait into an eggplant which may comprise a genetic determinant which when present leads to a trait of a reduced number of trichomes on vegetative plant parts, as compared to a plant not comprising the said genetic determinant, and which genetic determinant is as present in plants grown from seed, representative samples of which were deposited under accession numbers NCIMB 41756 and NCIMB 42013, which may comprise:

a) crossing an eggplant, that may comprise a genetic determinant which when present leads to a trait of a reduced number of trichomes on vegetative plant parts, as compared to a plant not comprising the said genetic determinant, and which genetic determinant is as present in plants grown from seed, representative samples of which were deposited under accession numbers NCIMB 41756 and NCIMB 42013, with a second eggplant that may comprise a desired trait to produce F1 progeny;
b) selecting an F1 progeny that may comprise said genetic determinant which when present leads to a trait of a reduced number of trichomes on vegetative plant parts and the desired trait;
c) crossing the selected F1 progeny with either parent, to produce backcross progeny;
d) selecting backcross progeny which may comprise the desired trait and the genetic determinant which when present leads to the trait of a reduced number of trichomes on vegetative plant parts; and
e) optionally repeating steps c) and d) one or more times in succession to produce selected fourth or higher backcross progeny that may comprise the desired trait and the genetic determinant which when present leads to the trait of a reduced number of trichomes on vegetative plant parts The invention includes an eggplant produced by this method.

In one embodiment selection for plants having the genetic determinant which when present leads to the trait of a reduced number of trichomes on vegetative plant parts is started in the F2 of a cross or alternatively of a backcross. Selection of plants in the F2 can be done phenotypically as well as by using the marker(s) which directly or indirectly detect the genetic determinant underlying the trait.

In one embodiment selection for plants, having the genetic determinant which when present leads to the trait of a reduced number of trichomes on vegetative plant parts, is started in the F3 or a later generation.

In one embodiment the plant which may comprise the genetic determinant, is a plant of an inbred line, a hybrid, a doubled haploid, or of a segregating population.

The invention further provides a method for the production of an eggplant having the genetic determinant which when present leads to the trait of a reduced number of trichomes on vegetative plant parts by using a doubled haploid generation technique to generate a doubled haploid line which may comprise the said trait.

The invention furthermore relates to hybrid seed that can be grown into a plant having the genetic determinant which when present leads to the trait of a reduced number of trichomes on vegetative plant parts, and to a method for producing such hybrid seed which may comprise crossing a first parent eggplant with a second parent eggplant and harvesting the resultant hybrid seed, wherein said first parent eggplant and/or said second parent eggplant is the plant as claimed.

In one embodiment, the invention relates to a method for producing a hybrid eggplant that has the genetic determinant which when present leads to the trait of a reduced number of trichomes on vegetative plant parts which may comprise crossing a first parent eggplant with a second parent eggplant and harvesting the resultant hybrid seed, of which the first parent plant and/or the second parent plant has the genetic determinant which when present leads to the trait of a reduced number of trichomes on vegetative plant parts and growing said hybrid seeds into hybrid plants having the genetic determinant which when present leads to the trait of a reduced number of trichomes on vegetative plant parts.

The invention also relates to a method for the production of an eggplant having the genetic determinant which when present leads to the trait of a reduced number of trichomes on vegetative plant parts by using a seed that may comprise a genetic determinant in its genome that leads to the trait of a reduced number of trichomes on vegetative plant parts for growing the said eggplant. The seeds are suitably seeds of which representative samples were deposited with the NCIMB under accession numbers NCIMB 41756 and NCIMB 42013.

The invention also relates to a method for seed production which may comprise growing eggplants from seeds of which representative samples were deposited with the NCIMB under accession numbers NCIMB 41756 and NCIMB 42013, allowing the plants to produce seeds, and harvesting those seeds. Production of the seeds is suitably done by crossing or selfing.

In one embodiment, the invention relates to a method for the production of an eggplant having the genetic determinant which when present leads to the trait of a reduced number of trichomes on vegetative plant parts by using tissue culture.

The invention furthermore relates to a method for the production of an eggplant, having the genetic determinant which when present leads to the trait of a reduced number of trichomes on vegetative plant parts, by using vegetative reproduction.

In one embodiment, the invention relates to a method for the production of an eggplant, having the genetic determinant which when present leads to the trait of a reduced number of trichomes on vegetative plant parts, by using a method for genetic modification to introgress the said trait into the eggplant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of eggplants, that have the genetic determinant which when present leads to the trait of a reduced number of trichomes on vegetative plant parts, wherein germplasm which may comprise said trait is used. Representative seed of said plant which may comprise the genetic determinant and being representative for the germplasm was deposited with the NCIMB under accession number NCIMB 41756 and NCIMB 42013.

In a further embodiment the invention relates to a method for the production of an eggplant having the genetic determinant which when present leads to the trait of a reduced number of trichomes on vegetative plant parts wherein progeny or propagation material of a plant which may comprise the genetic determinant conferring said trait is used as a source to introgress the said trait into another eggplant. Representative seed of said plant which may comprise the genetic determinant was deposited with the NCIMB under accession number NCIMB 41756 or NCIMB 42013.

The invention provides preferably an eggplant having the genetic determinant which when present leads to the trait of a reduced number of trichomes on vegetative plant parts, which plant is obtainable by any of the methods herein described and/or familiar to the skilled person.

The invention relates to a cell of an eggplant, which eggplant may comprise a genetic determinant which when present leads to a reduced number of trichomes on vegetative plant parts as compared to an eggplant not comprising the said genetic determinant, and is as found in an eggplant grown from seed, representative samples of which were deposited with NCIMB and under accession numbers NCIMB 41756 and NCIMB 42013. The cell of the eggplant may comprise the genetic determinant in its genome.

Another embodiment of the invention relates to a cell of an eggplant, which eggplant may comprise a genetic determinant which when present leads to a reduced number of trichomes on vegetative plant parts as compared to an eggplant not comprising said genetic determinant, and is as found in an eggplant grown from seed, of which representative samples were deposited with the NCIMB under accession numbers NCIMB 41756 and NCIMB 42013, which eggplant is obtainable by crossing an eggplant with an eggplant grown from seed, representative samples of which were deposited with the NCIMB under accession numbers NCIMB 41756 and NCIMB 42013, and selecting for an eggplant that shows a reduced number of trichomes on vegetative plant parts.

The invention also relates to use of seeds of which representative samples were deposited with the NCIMB under one of the accession numbers NCIMB 41756 and NCIMB 42013, for transferring the genetic determinant which when present in eggplant leads to a reduced number of trichomes on vegetative plant parts in eggplant as compared to an eggplant not comprising said genetic determinant, into another eggplant.

In another embodiment, the invention also relates to the use of an eggplant which eggplant may comprise a genetic determinant which when present leads to a reduced number of trichomes on vegetative plant parts as compared to an eggplant not comprising said genetic determinant, which genetic determinant is as found in an eggplant grown from seed of which representative samples were deposited with the NCIMB under one of the accession numbers NCIMB 41756 and NCIMB 42013, as a crop.

Furthermore, the invention relates to the use of an eggplant which may comprise a genetic determinant which when present leads to a reduced number of trichomes on vegetative plant parts as compared to an eggplant not comprising said genetic determinant, and which genetic determinant is as found in an eggplant grown from seed of which representative samples were deposited with NCIMB under one of the accession numbers NCIMB 41756 and NCIMB 42013, as a source of seed.

The invention further relates to the use of an eggplant which may comprise a genetic determinant which when present leads to a reduced number of trichomes on vegetative plant parts as compared to an eggplant not comprising said genetic determinant, and which genetic determinant is as found in an eggplant grown from seed of which representative samples were deposited with NCIMB, under one of the accession numbers NCIMB 41756 and NCIMB 42013, as a source of propagating material.

Another aspect of the invention relates to the use of an eggplant which may comprise a genetic determinant which when present leads to a reduced number of trichomes on vegetative plant parts as compared to an eggplant not comprising said genetic determinant, which genetic determinant is as found in an eggplant grown from seed of which representative samples were deposited with NCIMB under one of the accession numbers NCIMB 41756 and NCIMB 42013, for consumption.

Furthermore, the invention relates to the use of reduced number of trichomes eggplant alleles as found in eggplant seeds of which representative samples were deposited with the NCIMB under one of the accession numbers NCIMB 41756 and NCIMB 42013, for conferring the trait a reduced number of trichomes on vegetative plant parts in an eggplant as compared to an eggplant not comprising said alleles, on an eggplant.

Moreover, the invention also relates to the use of an eggplant as a recipient of the reduced number of trichomes eggplant alleles as found in seeds of which representative samples were deposited with NCIMB under one of the accession numbers NCIMB 41756 and NCIMB 42013.

The term "is as present in" as used in this application in the context of the genetic determinant means to refer to a genetic determinant that is the same or similar as the gene or genes that causes/cause the trait of a reduced number of trichomes on vegetative parts of an eggplant. "The same or similar or equivalent" is intended to mean that the function of the gene or genes is the same. In practice this will usually mean that the DNA sequence of the gene or genes is identical to the gene or genes that are present in the genome of the deposited material or allelic to this gene, i.e. only so much different therefrom that the function of the gene or genes in causing the trait is still intact.

The reduced number of trichomes leads to a hairless phenotype. The phrase "a reduced number of trichomes" and the word "hairless" may be used interchangeably.

Seeds of *Solanum melongena* plants with the genetic determinant that confers the scarcity of trichomes/reduced number of trichomes on vegetative plant parts of the invention were deposited under NCIMB accession number NCIMB 41756 on 22 Sep. 2010 at NCIMB Ltd. (Ferguson Building, Craibstone Estate, Bucksburn, Aberdeen, AB21 9YA) and NCIMB accession number NCIMB 42013 on 19 Jul. 2012 with the NCIMB Ltd. (Ferguson Building, Craibstone Estate, Bucksburn, Aberdeen, AB21 9YA). All seeds of these deposits may comprise the genetic determinant homozygously. Plants grown from these seeds show a strongly reduced number of trichomes per square centimeter on vegetative plant parts as compared to plants not comprising the genetic determinant. The seeds are a representative sample of seeds capable of growing into plants that show the reduced number of trichomes on vegetative plant parts. The present invention is not limited to the deposited seeds but extends to all seeds that have the same or a similar genetic determinant that leads to the reduced number of trichomes as the deposited seeds and plants grown therefrom.

The invention will now be elucidated in the Examples that follow and that are only given for illustrative purposes and are in no way intended to be limiting on the scope of the invention. In the Examples reference is made to the following figures:

FIG. 1 Photograph of a leaf with normal trichome density.

Figure 2:
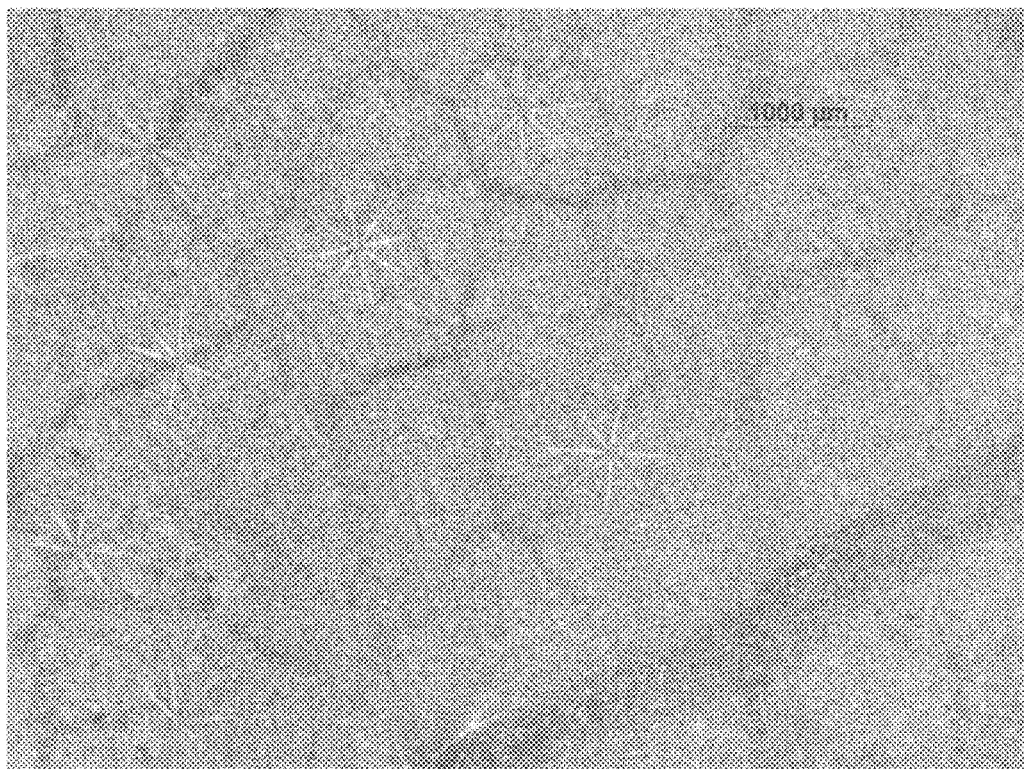
FIG. 2 Photograph of a leaf with a reduced number of trichomes.

FIG. 2 Photograph of a leaf with a reduced number of trichomes.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLE 1

Analysis of Hairless Eggplants

Seeds of the eggplant of the invention and control plants were sown in rockwool at 23° C. (about 16 hours light/8 hours darkness). After germination the seedlings were transferred to rockwool cubes and were grown in the greenhouse at a temperature of 21° C. After seven weeks the plants were checked for trichomes, and the trichomes were counted. All trichome counts were made on a surface of one square centimeter.

All trichome counts were made on the same day, on both immature and mature leafs. The samples of the young leaf were taken on the first leaf from the top of the plant that measured 5 centimeter in length. The sample of the mature leaf was taken from the first stretched leaf seen from the top of the plant. In general this was the third leaf under the leaf that we defined as 'young leaf'. For each genotype, five plants were sampled. For each mature leaf, two counts were made on the underside of the leaf blade and two counts were made on the upperside of the leaf stalk. For each young leaf also two counts were made on the underside of the leaf blade plus two counts on the underside of the leaf stalk. In addition, two counts on the main stem were made, between the fourth and the fifth leaf counted from the basis of the plant. These counts were averaged for each genotype. The results of the counts are shown in Table 1. The results show that the number of trichomes on plants of the deposit is strongly reduced compared to the number of trichomes on reference plants derived from varieties "Thelma" and "Elisa".

The eggplant variety "Elisa" is registered at The NAKtuinbouw Institute in the Netherlands, as an eggplant variety with less trichomes than normal on the main stem. The difference between these reference plants and plants of the deposit is most obvious in the counts on the mature leaf blade/lamina, there is around a tenfold reduction of trichomes per square centimeter in the plants of the deposits compared to the reference genotypes Elisa and Thelma.

TABLE 1

Number of trichomes per square centimeter plant surface

| Genotype | Mature leaf, lamina | Mature leaf, leafstalk | Young leaves, lamina | Young leaves, leafstalk | main stem |
|---|---|---|---|---|---|
| Deposit (F1) NCIMB 41756 | 7 | 10 | 76.2 | 22.6 | 0.4 |
| Deposit (F1) NCIMB 42013 | 16.3 | 11.8 | 68.5 | 10.8 | 2.1 |
| hairy reference Elisa F1 | 142.7 | 37.4 | 585.9 | 63.6 | 9.9 |
| hairy reference Thelma F1 | 196.5 | 96.4 | 615.4 | 300.8 | 66.6 |

EXAMPLE 2

Evaluation of the Effect of a Reduced Number of Trichomes on Infestation with White Flies and their Natural Predator the Predatory Mite *Amblyseius swirskii*

In an experiment executed with two different eggplant genotypes, a control plant derived from variety "Thelma" having a normal number of trichomes on the vegetative plant parts and a plant of deposit NCIMB 41756, which may comprise the genetic determinant that leads to the reduced number of trichomes on vegetative plant parts (abbreviation NCIMB 41756), the effects of an infestation with whitefly (*Bemisia tabaci*) and whitefly in combination with its natural enemy the predatory mite (*Amblyseius swirskii*) were studied. The experiment was conducted in twelve insect-free gauze cages within a greenhouse. Four different treatments times three replicates were evaluated. The four treatments were: Plants from "Thelma" with biological pest control, plants from "Thelma" without biological pest control, plants from deposit NCIMB 41756 with biological pest control, plants from deposit NCIMB 41756 without biological pest control.

In all the treatments, the plants were infested with adults of white flies about 45 days after planting of the seedlings. On each plant 10 adult white flies were placed. The plants in the biological pest control experimental units received at the same day the predatory mites (a quantity of 100 predatory mites per plant). For 16 weeks, observations were done and different variables were recorded. Observations were made on 10 different plants in each experimental unit (cage). For each plant, observations were made on three different leafs on three different levels of the plant (low, medium, high) plus on one flower. The following parameters were evaluated: number of predatory mites, number of larvae/pupae of mites, number of pupae of the white fly, number of parasitized pupae of white fly, number of adult white fly. The data were analyzed and the most important results are shown in Table 2.

Based on these results, the following conclusions were drawn. Within both treatments (with and without biological pest control) the numbers of white fly adults, nymphs and pupae were highest in plants of the control variety "Thelma". Overall the lowest white fly infestation was found in plants from deposit NCIMB 41756 with biological pest control. In the two treatments with biological pest control, the lowest number of white flies, both white fly nymphs and pupae as well as white fly adults were found on plants from deposit NCIMB 41756. Without wishing to be bound by theory one of the underlying causes for this phenomena could be that search time for prey is less on plants with a reduced number of trichomes, and that the predatory mites because of this advantage, have a higher reproduction than on plants with hairy leaves.

TABLE 2

Average number of insects a day per plant, accumulated for all 16 consecutive observations (16 weeks) for each treatment; BPC = Biological pest control

| Treatment | White fly nymphs and pupae | White fly adults | Predatory mites A. swirskii adults |
|---|---|---|---|
| "Thelma" | 1377.7 | 795.2 | n.a. |
| "Thelma" with BPC | 431.5 | 219.1 | 101.5 |
| NCIMB 41756 | 786.6 | 555.5 | n.a. |
| NCIMB 41756 with BPC | 41.0 | 55.6 | 138.9 |

EXAMPLE 3

Transfer of the Trait of the Invention to other Eggplants

The eggplants which may comprise the genetic determinant for the trait a reduced number of trichomes on vegetative plant parts as found in representative seed as deposited under accession number NCIMB 41756 (called herein the donor) were used to transfer the trait of a reduced number of trichomes on vegetative plant parts by crossing to the parents (mother and father) of cultivated eggplant called "Thelma", in order to make a plant resembling Thelma, but with the trait of a reduced number of trichomes on vegetative plant parts.

After obtaining the F1 seeds, they were sown and the plants grown from the F1 seeds were selfed. The plants of the subsequent F2 populations were visually screened for the phenotype of a reduced number of trichomes on vegetative plant parts. The plantlets expressing the trait of a reduced number of trichomes on vegetative plant parts were selected. These selected plants were crossed again with the same parent (recurrent parent) of cultivated eggplant variety Thelma. The BC1 populations thus obtained were propagated into F2BC1 populations, which were again visually screened for the phenotype a reduced number of trichomes on vegetative plant parts plant parts.

The F2BC1 eggplants with the preferred trait were selected and crossed again with its recurrent parent. By performing this recurrent breeding process (also called backcrossing) the agronomic properties of the breeding material is improved and in the end the preferred trait of a reduced number of trichomes on vegetative plant parts is obtained in the parents of a cultivated eggplant variety.

The improved cultivated eggplant variety with the preferred trait of a reduced number of trichomes on vegetative plant parts is made by crossing the improved mother and father line.

EXAMPLE 4

Skin Irritation in Human Volunteers

In an experiment 8 healthy adult volunteers, 4 women, 4 men, were exposed to freshly harvested eggplant leafs. Each of the volunteers received two big (>20 cm in length) eggplant leafs. One leaf had normal trichome density and was harvested from a control plant. The other leaf with reduced number of trichomes was harvested from plants of the invention, as deposited under NCIMB number NCIMB 41756. The leaves were lightly rubbed to the bare lower part of the arm of the volunteers by the volunteers themselves. Each leaf was used for only one arm of the volunteer, which means that the leaf with trichomes was applied to a different arm than the leaf with almost no trichomes. The reactions of the skin of the arm and the sensation by the volunteers were noted on 3 different stages, at the moment of applying the leaf to the arm, 15 minutes after the application and 30 minutes after application.

As shown in Table 3, most volunteers felt an itching sensation on the skin being exposed to the leaf or their skin turned red (without scratching) after application of the hairy eggplant leaf. In some volunteers, it took up to 30 minutes to develop these symptoms while in others, the itching started immediately. The plants from the invention did not result in itching or visible skin irritation in most of the volunteers, 2 individuals excepted. However, one of these individuals with a reaction to both leaves had already been exposed to eggplants with hairs earlier that day.

TABLE 3

Skin reaction in human volunteers during and after exposure with mature eggplant leaves with and (almost) without trichomes

| skin reaction test d.d.31 July 2012 | male/ female | itch/ redness after 0 minutes hairy | invention | itch/ redness after 15 minutes hairy | invention | itch/ redness after 30 minutes hairy | invention |
|---|---|---|---|---|---|---|---|
| person C | female | no | no | yes | no | yes | no |
| person A | male | yes | no | no | no | yes | no |
| person K | male | no | no | no | no | yes | no |
| person M | female | no | no | no | no | yes | no |
| person ME | male | yes | no | yes | yes | yes | yes |
| person L | female | yes | yes | yes | yes | yes | yes |
| person B | male | no | no | yes/no | no | yes | no |
| person CH | female | no | no | yes/no | no | yes | no |

The invention is further described by the following numbered paragraphs:

1. An eggplant, comprising a genetic determinant which when present leads to a trait of a reduced number of trichomes on vegetative plant parts, in particular leafs, stems and calyx, as compared to a plant not comprising the said genetic determinant, and wherein the genetic determinant is the same as or equivalent to a genetic determinant present in the genome of plants grown from seed which were deposited under accession numbers NCIMB 41756 and NCIMB 42013.

2. The eggplant as in paragraph 1, wherein the eggplant is of the species *Solanum melongena* L.

3. The eggplant as in paragraph 1 or 2, wherein the genetic determinant is homozygously present.

4. The eggplant as in any one of the paragraphs 1-3 wherein the genetic determinant is obtainable from seed, representative samples of which were deposited under accession numbers NCIMB 41756 and NCIMB 42013.

5. An eggplant as in any one of the paragraphs 1 to 4, wherein the plant is obtainable by crossing a first eggplant not having the genetic determinant, with a second eggplant having the genetic determinant, or by introgression of the genetic determinant into the first eggplant from the second eggplant, wherein the genetic determinant is the same as or equivalent to a genetic determinant present in the genome of plants grown from seed which were deposited under accession numbers NCIMB 41756 and NCIMB 42013.

6. An eggplant of the species *Solanum melongena* which has a reduced number of trichomes on vegetative plant parts, in particular leafs, stems and calyx, as compared to a control plant, which plant is obtainable by crossing an eggplant of NCIMB 41756 or NCIMB 42013 with another eggplant and selecting in the first or further progeny of the cross for plants having a reduced number of trichomes.

7. An eggplant as in any one of the paragraphs 1 to 6, wherein leaf blades of the mature leaves of the eggplant have less than 130 trichomes per square centimeter, preferably less than 120 trichomes per square centimeter, more preferably less than 110 trichomes per square centimeter, even more preferably less than 100 trichomes per square centimeter, even more preferably less than 90 trichomes per square centimeter, even more preferably less than 80 trichomes per square centimeter, even more preferably less than 70 trichomes per square centimeter, even more preferably less than 60 trichomes per square centimeter, even more preferably less than 50 trichomes per square centimeter, even more preferably less than 40 trichomes per square centimeter, even more preferably less than 30 trichomes per square centimeter, even more preferably less than 20 trichomes per square centimeter, even more preferably less than 10 trichomes per square centimeter, even more preferably less than 5 trichomes per square centimeter, most preferably 0 trichomes per square centimeter.

8. Seed of an eggplant as defined in any one of the paragraphs 1 to 7, comprising the genetic determinant as defined in paragraph 1 which when present leads to a trait of a reduced number of trichomes on vegetative plant parts in a plant grown from the seed as compared to a plant grown from seed not comprising the genetic determinant.

9. Seed of an eggplant as in paragraph 8, wherein the genetic determinant is homozygously present and the plant grown from the seed shows a strongly reduced number of trichomes on vegetative plant parts as compared to a plant grown from seed not comprising the genetic determinant.

10. Progeny plant of an eggplant as in any one of the paragraphs 1 to 6 or of a plant grown from seed as in paragraph 8 and 9, wherein the progeny plant comprises the genetic determinant as defined in paragraph 1 and shows a reduced number of trichomes on vegetative plant parts as compared to a plant not comprising the genetic determinant.

11. Progeny plant as in paragraph 10 wherein the genetic determinant is homozygously present and the progeny plant shows a strongly reduced number of trichomes on vegetative plant parts as compared to a plant not comprising the genetic determinant.

12. Propagation material derived from a plant as in any one of the paragraphs 1 to 7 and 10 and 11 wherein the propagation material comprises the genetic determinant as defined in paragraph 1.

13. Propagation material capable of growing into a plant as in any one of the paragraphs 1 to 7.

14. Propagation material as in paragraph 12 or 13, wherein the propagation material is selected from the group consisting of microspores, pollen, ovaries, ovules, embryos, embryo sacs, egg cells, cuttings, roots, stems, cells, protoplasts, leaves, cotyledons, hypocotyls, meristematic cells, roots, root tips, microspores, anthers, flowers, seeds and stems or parts thereof.

15. Tissue culture of propagation material as in any one of the paragraphs 12-14.

16. An eggplant fruit, or parts thereof, or a food product made of a fruit or of parts thereof, or a processed food product made thereof, harvested from an eggplant as in any one of the paragraphs 1 to 7.

17. The use of an eggplant as in any one of the paragraphs 1 to 7 as germplasm in a breeding program for the development of eggplants comprising the genetic determinant as defined in paragraph 1 that leads to a reduced number of trichomes on vegetative parts of the plant, as compared to a plant not carrying said determinant.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. An eggplant of the species *Solanum melongena* L., wherein leaf blades of the mature leaves of the eggplant have less than 20 trichomes per square centimeter, representative seed of which having been deposited under accession number NCIMB 41756 or NCIMB 42013.

2. A method of producing an eggplant of the species *Solanum melongena* L., wherein leaf blades of the mature leaves of the *Solanum melongena* L. plant have less than 20 trichomes per square centimeter, comprising:

crossing an eggplant, representative seed of which having been deposited as NCIMB 41756 or NCIMB 42013, with another eggplant and selecting in the F1 of the cross for plants of which the leaf blades of the mature leaves have less than 20 trichomes per square centimeter;

crossing an eggplant, representative seed of which having been deposited as NCIMB 41756 or NCIMB 42013, with another eggplant to obtain an F1, selfing the resulting F1 for obtaining F2 plants, and selecting in the F2 for plants of which the leaf blades of the mature leaves have less than 20 trichomes per square centimeter;

or crossing an eggplant, representative seed of which having been deposited as NCIMB 41756 or NCIMB 42013 with another eggplant to obtain an F1, backcrossing the resulting F1 with an eggplant, representative seed of which having been deposited as NCIMB 41756 or NCIMB 42013, obtaining F2 plants from the backcross, and selecting F2 plants wherein the leaf blades of the mature leaves have less than 20 trichomes per square centimeter, and optionally performing one or more rounds of selfing or backcrossing and subsequently selecting for plants wherein the leaf blades of the mature leaves have less than 20 trichomes per square centimeter.

3. The eggplant as claimed in claim 1, wherein leaf blades of the mature leaves of the eggplant have less than 10 trichomes per square centimeter, less than 5 trichomes per square centimeter, or 0 trichomes per square centimeter.

4. A seed capable of growing into the eggplant of claim 1.

5. A propagation material capable of growing into the plant of claim 1.

6. The propagation material of claim 5, wherein the propagation material is a microspore, pollen, ovary, ovule, embryo, embryo sac, egg cell, cutting, root, stem, cell, protoplast, leaf, cotyledon, hypocotyl, meristematic cell, root, root tip, microspore, anther, flower, seed, stem or a part thereof.

7. A tissue culture of the propagation material of claim 5.

8. An eggplant fruit or a food product comprising said fruit, harvested from the eggplant of claim 1.

9. A method of developing an eggplant of the species *Solanum melongena* L. wherein leaf blades of the mature leaves of the eggplant have less than 20 trichomes per square centimeter, comprising a) crossing the eggplant of claim 1 with another plant;
b) selfing the resulting F1 for obtaining F2 plants;
c) selecting plants of which the leaf blades of the mature leaves have less than 20 trichomes per square centimeter in the F2; and
d) optionally performing one or more additional rounds of selfing or backcrossing, and subsequently selecting, for a plant of which the leaf blades of the mature leaves comprise/show less than 20 trichomes per square centimeter.

10. An F1 seed or F1 progeny plant produced by crossing the plant of claim 1 with a different *Solanum melongena* plant.

* * * * *

UNITED STATES PATENT AND TRADEMARK OFFICE
CERTIFICATE OF CORRECTION

PATENT NO. : 10,349,612 B2
APPLICATION NO. : 14/628169
DATED : July 16, 2019
INVENTOR(S) : Johannes Henricus Jacobus Van Den Enden et al.

Page 1 of 1

It is certified that error appears in the above-identified patent and that said Letters Patent is hereby corrected as shown below:

In the Claims

Please amend Claim 2, at Column 19, Line 31 as follows:
2. A method of producing an eggplant of the species Solanum melongena L., wherein leaf blades of the mature leaves of the Solanum melongena L. plant have less than 20 trichomes per square centimeter, comprising: crossing an eggplant, representative seed of which having been deposited as NCIMB 41756 or NCIMB 42013, with another eggplant and selecting in the F1 of the cross for plants of which the leaf blades of the mature leaves have less than 20 trichomes per square centimeter; crossing an eggplant, representative seed of which having been deposited as NCIMB 41756 or NCIMB 42013, with another eggplant to obtain an F1, selfing the resulting F1 for obtaining F2 plants, and selecting in the F2 for plants of which the leaf blades of the mature leaves have less than 20 trichomes per square centimeter; or crossing an eggplant, representative seed of which having been deposited as NCIMB 41756 or NCIMB 42013 with another eggplant to obtain an F1, backcrossing the resulting F1 with an eggplant, representative seed of which having been deposited as NCIMB 41756 or NCIMB 42013, obtaining F2 plants from the backcross, and selecting F2 plants wherein the leaf blades of the mature leaves have less than 20 trichomes per square centimeter, and optionally performing one or more rounds of selfing or backcrossing and subsequently selecting for plants wherein the leaf blades of the mature leaves have less than 20 trichomes per square centimeter.

Please correct Claim 8, at Column 20, Line 22 as follows:
8. An eggplant fruit or a food product comprising said fruit harvested from the eggplant of claim 1.

Signed and Sealed this
Twenty-fourth Day of September, 2019

Andrei Iancu
*Director of the United States Patent and Trademark Office*